United States Patent [19]
Dubief et al.

[11] Patent Number: 5,976,517
[45] Date of Patent: Nov. 2, 1999

[54] HAIR CARE COMPOSITION INCLUDING AT LEAST ONE SILICONE POLYMER GRAFTED BY ANIONIC, AMPHOTERIC OR NON-IONIC MONOMERS, AND AT LEAST ONE AMPHOTERIC POLYMER

[75] Inventors: Claude Dubief, Le Cheaney; Christine Dupuis; Daniele Cauwet-Martin, both of Paris, all of France

[73] Assignee: L'Oreal, Paris, France

[21] Appl. No.: 08/983,339

[22] PCT Filed: Sep. 16, 1996

[86] PCT No.: PCT/FR96/01440

§ 371 Date: Dec. 30, 1997

§ 102(e) Date: Dec. 30, 1997

[87] PCT Pub. No.: WO97/12596

PCT Pub. Date: Apr. 10, 1997

[30] Foreign Application Priority Data

Sep. 29, 1995 [FR] France ................................. 95 11488

[51] Int. Cl.⁶ .............................. A61K 7/06; A61K 7/11; A61K 31/74
[52] U.S. Cl. .................. 424/70.1; 424/70.12; 424/78.03
[58] Field of Search ............................. 424/70.12, 70.11, 424/78.03

[56] References Cited

FOREIGN PATENT DOCUMENTS

| 0 582 152 | 2/1994 | European Pat. Off. |
| 2 709 955 | 3/1995 | France . |
| WO 91/15186 | 10/1991 | WIPO . |
| WO 95/00108 | 1/1995 | WIPO . |

OTHER PUBLICATIONS

English Language Derwent Abstract of FR 2 709 955.

*Primary Examiner*—Carlos A. Azpuru
*Attorney, Agent, or Firm*—Finnegan, Henderson, Farabow, Garrett & Dunner, L.L.P.

[57] ABSTRACT

A cosmetic or dermatological composition for treating keratinous material, particularly human hair, including a cosmetically or dermatologically acceptable medium containing at least one anionic, amphoteric or non-ionic silicone-grafted polymer with a polysiloxane backbone grafted by non-silicone organic monomers, and at least one amphoteric polymer, wherein the ratio of the amphoteric polymer to the silicone-grafted polymer is 0.25–15. Such compositions are particularly suitable for use as rinsable or non-rinsable products for washing and conditioning hair, hair setting or hair styling.

46 Claims, No Drawings

HAIR CARE COMPOSITION INCLUDING AT LEAST ONE SILICONE POLYMER GRAFTED BY ANIONIC, AMPHOTERIC OR NON-IONIC MONOMERS, AND AT LEAST ONE AMPHOTERIC POLYMER

The present invention relates to a cosmetic or dermatological composition for treating keratin substances, in particular human hair, comprising at least one grafted silicone polymer containing a polysiloxane skeleton grafted with anionic, amphoteric or nonionic non-silicone organic monomers and at least one amphoteric polymer.

Grafted silicone polymers are known in the prior art, such as those described in patent applications EP-A-0,582, 152 and WO 93/23009. These polymers are proposed in hair composition for their styling properties. However, when these polymers are used, the fixing power of the composition and the feel of the hair are unsatisfactory.

The Applicant has discovered, surprisingly, that by combining at least one grafted silicone polymer of the anionic, amphoteric or nonionic type with at least one amphoteric polymer in an amphoteric polymer/grafted silicone polymer ratio of between 0.25 and 15, the softness and feel properties of hair are substantially superior to those obtained with each polymer used alone.

The composition according to the invention is thus essentially characterized in that it comprises, in a cosmetically or dermatologically acceptable medium, at least one grafted silicone polymer containing a polysiloxane skeleton grafted with non-silicone organic monomers of the anionic, amphoteric or nonionic type and at least one amphoteric polymer, in an amphoteric polymer/grafted silicone polymer ratio of between 0.25 and 15.

In the following text, in accordance with what is generally accepted, the term silicone polymer is understood to denote any organosilicon polymer or oligomer having a linear or cyclic, branched or crosslinked structure of variable molecular weight, obtained by polymerization and/or polycondensation of suitably functionalized silanes, and consisting essentially of a repetition of main units in which the silicon atoms are linked together by oxygen atoms (siloxane bonding $\equiv$Si—O—Si$\equiv$), optionally substituted hydrocarbon radicals being linked directly via a carbon atom to the said silicon atoms. The most common hydrocarbon radicals are alkyl radicals, especially $C_1$–$C_{10}$ alkyl radicals, and in particular methyl, fluoroalkyl radicals, aryl radicals and in particular phenyl, and alkenyl radicals and in particular vinyl; other types of radicals which can be linked, either directly or via a hydrocarbon radical, to the siloxane chain are, especially, hydrogen, halogens and in particular chlorine, bromine or fluorine, thiols, alkoxy radicals, polyoxyalkylene (or polyether) radicals and in particular polyoxyethylene and/or polyoxypropylene, hydroxyl or hydroxyalkyl radicals, amide groups, acyloxy radicals or acyloxyalkyl radicals, amphoteric or betaine groups, anionic groups such as carboxylates, thioglycolates, sulphosuccinates, thiosulphates, phosphates and sulphates, needless to say this list not being limiting in any way (so-called "organomodified" silicones).

According to the present invention, the silicone polymer (s) which must be used is (are) that (those) which comprise (s) a main silicone chain (or polysiloxane ($\equiv$Si—O—)$_n$) on which is grafted, inside the said chain as well as, optionally, on at least one of its ends, at least one organic group containing no silicone.

These silicone polymers can be existing commercial products or can be obtained according to any means known to those skilled in the art, in particular by reaction between (i) a starting silicone which is correctly functionalized on one or more of these silicon atoms, and (ii) a non-silicone organic compound which is itself correctly functionalized with a function which is capable of reacting with the functional group(s) borne by the said silicone, forming a covalent bond; a classic example of such a reaction is the hydrosilylation reaction between $\equiv$Si—H groups and vinyl groups $CH_2$=CH—, or alternatively the reaction between thio functional groups —SH with these same vinyl groups.

Examples of silicone polymers which are suitable for carrying out the present invention, as well as their specific mode of preparation, are described in particular in patent applications EP-A-0,582,152, WO 93/23009 and WO 95/03776, the teachings of which are included in their entirety in the present description by way of non-limiting references.

According to a particularly preferred embodiment of the present invention, the silicone polymer which is used comprises the result of the radical copolymerization between, on the one hand, at least one non-silicone anionic organic monomer having ethylenic unsaturation and/or a non-silicone hydrophobic organic monomer having ethylenic unsaturation, and, on the other hand, a silicone having in its chain at least one functional group capable of reacting with the said ethylenic unsaturations of the said non-silicone monomers, forming a covalent bond, in particular thio functional groups.

According to the present invention, the said anionic monomers containing ethylenic unsaturation are preferably chosen, alone or as a mixture, from linear or branched, unsaturated carboxylic acids, optionally partially or totally neutralized in the form of a salt, it being possible for this (these) carboxylic acid(s) to be, more particularly, acrylic acid, methacrylic acid, maleic acid, maleic anhydride, itaconic acid, fumaric acid and crotonic acid. The suitable salts are, in particular, alkali metal salts, alkaline-earth metal salts and ammonium salts. It will likewise be noted that, in the final grafted silicone polymer, the organic group of anionic nature which comprises the result of the radical (homo) polymerization of at least one anionic monomer of unsaturated carboxylic acid type can, after reaction, be post-neutralized with a base (sodium hydroxide, aqueous ammonia, etc) in order to bring it into the form of a salt.

According to the present invention, the hydrophobic monomers containing ethylenic unsaturation are preferably chosen, alone or as a mixture, from acrylic acid esters of alkanols and/or methacrylic acid esters of alkanols. The alkanols are preferably $C_1$–$C_{18}$ and more particularly $C_1$–$C_{12}$. The preferred monomers are chosen from the group consisting of isooctyl (meth)acrylate, isononyl (meth) acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth) acrylate, tridecyl (meth)acrylate and stearyl (meth)acrylate, or mixtures thereof.

One family of grafted silicone polymers which is particularly suitable for carrying out the present invention consists of silicone polymers containing in their structure the unit of formula (I) below:

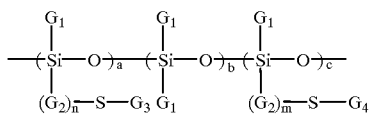
(I)

in which the radicals $G_1$, which may be identical or different, represent hydrogen or a $C_1$–$C_{10}$ alkyl radical or alternatively a phenyl radical; the radicals $G_2$, which may be identical or different, represent a $C_1$–$C_{10}$ alkylene group; $G_3$ represents a polymer residue resulting from the (homo)polymerization of at least one anionic monomer containing ethylenic unsaturation; $G_4$ represents a polymer residue resulting from the (homo)polymerization of at least one hydrophobic monomer containing ethylenic unsaturation; m and n are equal to 0 or 1; a is an integer ranging from 0 to 50; b is an integer which may be between 10 and 350, c is an integer ranging from 0 to 50; with the proviso that one of the parameters a and c is other than 0.

Preferably, the unit of formula (I) above has at least one, and even more preferably all, of the following characteristics:

the radicals $G_1$ denote an alkyl radical, preferably the methyl radical;

n is non-zero and the radicals $G_2$ represent a divalent $C_1$–$C_3$ radical, preferably a propylene radical;

$G_3$ represents a polymeric radical resulting from the (homo)polymerization of at least one monomer of the carboxylic acid type containing ethylenic unsaturation, preferably acrylic acid and/or methacrylic acid;

$G_4$ represents a polymeric radical resulting from the (homo)polymerization of at least one monomer of the $C_1$–$C_{10}$ alkyl (meth)acrylate type, preferably of the isobutyl or methyl (meth)acrylate type.

Examples of silicone polymers corresponding to formula (I) are, in particular, polydimethylsiloxanes (PDMS) on which are grafted, via a thiopropylene-type connecting chain, mixed polymer units of the poly(meth)acrylic acid type and of the polymethyl (meth)acrylate type.

Other examples of silicone polymers corresponding to formula (I) are, in particular, polydimethylsiloxanes (PDMS) on which are grafted, via a thiopropylene-type connecting chain, polymer units of the polyisobutyl (meth) acrylate type.

Preferably, the number-average molecular mass of the silicone polymers of the invention, ranges approximately from 10,000 to 1,000,000 and even more preferably approximately from 10,000 to 100,000.

The grafted silicone polymer in accordance with the invention is preferably used in an amount ranging from 0.01 to 20% by weight relative to the total weight of the composition. More preferably, this amount ranges from 0.1 to 15% by weight and even more particularly from 0.5 to 10% by weight.

According to the invention, any amphoteric polymer known per se can be used. These polymers are preferably fixing polymers, that is to say polymers having the function of temporarily fixing the shape of the hairstyle.

Needless to say, one or more amphoteric polymers can be used.

The amphoteric polymers which can be used in accordance with the invention can be chosen from polymers containing units A and B randomly distributed in the polymer chain, in which A denotes a unit derived from a monomer containing at least one basic nitrogen atom and B denotes a unit derived from an acidic monomer containing one or more carboxylic or sulphonic groups, or alternatively A and B can denote groups derived from zwitterionic monomers of carboxybetaines or of sulphobetaines; A and B can also denote a cationic polymer chain containing primary, secondary, tertiary or quaternary amine groups, in which at least one of the amine groups bears a carboxylic or sulphonic group connected via a hydrocarbon radical, or alternatively A and B form part of a chain of a polymer containing an α,β-dicarboxylic ethylene unit in which one of the carboxylic groups has been reacted with a polyamine containing one or more primary or secondary amine groups.

The amphoteric polymers corresponding to the definition given above which are more particularly preferred are chosen from the following polymers:

(1) polymers resulting from the copolymerization of a monomer derived from a vinyl compound bearing a carboxylic group such as, more particularly, acrylic acid, methacrylic acid, maleic acid or α-chloroacrylic acid, and of a basic monomer derived from a substituted vinyl compound containing at least one basic atom such as, more particularly, dialkylaminoalkyl methacrylate and acrylate, dialkylaminoalkyl methacrylamide and acrylamide. Such compounds are described in U.S. Pat. No. 3,836,537.

(2) polymers derived from diallyldialkylammonium and from at least one anionic monomer, such as polymers containing from about 60 to about 99% by weight of units derived from a quaternary diallyldialkylammonium monomer in which the alkyl groups are chosen, independently, from alkyl groups having 1 to 18 carbon atoms and in which the anion is derived from an acid having an ionization constant of greater than $10^{-13}$ and 1 to 40% by weight of this polymer, of an anionic monomer chosen from acrylic or methacrylic acid, the molecular weight of this polymer being approximately between 50,000 and 10,000,000, determined by gel permeation chromatography. Such polymers are described in patent application EP-A-269,243.

The preferred polymers are, inter alia, polymers containing alkyl groups chosen from groups having 1 to 4 carbon atoms and more particularly methyl and ethyl groups.

Among these polymers, copolymers of dimethyldiallylammonium chloride or of diethyldiallylammonium chloride and of acrylic acid are particularly preferred. These polymers are sold, for example, under the names "Merquat 280" and "Merquat 295" by the company Merck.

The terpolymers of dimethyldiallyammonium chloride/acrylic acid/acrylamide sold under the name "MERQUAT PLUS 3330" by the company Merck can also be used.

(3) polymers containing units derived:
a) from at least one monomer chosen from acrylamides or methacrylamides substituted on the nitrogen with an alkyl radical,
b) from at least one acidic comonomer containing one or more reactive carboxylic groups, and
c) from at least one basic comonomer such as esters containing primary, secondary, tertiary and quaternary amine substituents of acrylic acid and methacrylic acid and the quaternization product of dimethylaminoethyl methacrylate with dimethyl or diethyl sulphate.

The N-substituted acrylamides or methacrylamides more particularly preferred according to the invention are groups in which the alkyl radicals contain from 2 to 12 carbon atoms, and more particularly N-ethylacrylamide, N-tert-butylacrylamide, N-tert-octylacrylamide, N-octylacrylamide, N-decylacrylamide and N-dodecylacrylamide, as well as the corresponding methacrylamides.

The acidic comonomers are chosen more particularly from acrylic acid, methacrylic acid, crotonic acid, itaconic acid, maleic acid and fumaric acid as well as monoesters of alkyl having 1 to 4 carbon atoms of maleic or fumaric acid or anhydride.

The preferred basic comonomers are aminoethyl, butylaminoethyl, N,N'-dimethylaminoethyl and N-tert-butylaminoethyl methacrylates. The copolymers whose CTFA name (4th edition, 1991) is octylacrylamide/acrylates/butylaminoethyl methacrylate copolymer, such as the products sold under the name Amphomer or Lovocryl 47 by the company National Starch, are particularly used.

(4) partially or totally alkylated and crosslinked polyamino amides derived from polyamino amides of general formula:

in which $R_{10}$ represents a divalent radical derived from a saturated dicarboxylic acid, from an aliphatic mono- or dicarboxylic acid containing an ethylenic double bond, from an ester of a lower alkanol having 1 to 6 carbon atoms of these acids or from a radical derived from the addition of any one of the said acids to a bis-primary or bis-secondary amine, and Z denotes a radical of a bis-primary, mono- or bis-secondary polyalkylene polyamine and preferably represents:

a) in proportions of 60 to 100 mol %, the radical

where x=2 and n=2 or 3 or alternatively x=3 and n=2 this radical being derived from diethylenetriamine, triethylenetetraamine or dipropylenetriamine;

b) in proportions of 0 to 40 mol %, the radical (III) above, in which x=2 and n=1 and which is derived from ethylenediamine, or the radical derived from piperazine:

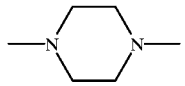

c) in proportions of 0 to 20 mol %, the radical —NH—$(CH_2)_6$—NH— derived from hexamethylenediamine, these polyamino amides being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid, 2,4,4-trimethyladipic acid, terephthalic acid and acids containing an ethylenic double bond such as, for example, acrylic acid, methacrylic acid or itaconic acid. The alkane sultones used in the alkylation are preferably propane sultone or butane sultone, and the salts of the alkylating agents are preferably the sodium or potassium salts.

(5) polymers containing zwitterionic units of formula:

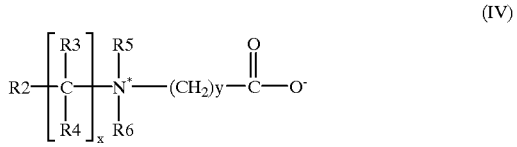

in which $R_2$ denotes a polymerizable unsaturated group such as an acrylate, methacrylate, acrylamide or methacrylamide group, x and y represent an integer from 1 to 3, $R_3$ and $R_4$ represent hydrogen, methyl, ethyl or propyl, $R_5$ and $R_6$ represent a hydrogen atom or an alkyl radical such that the sum of the carbon atoms in $R_5$ and $R_6$ does not exceed 10.

The polymers comprising such units can also contain units derived from non-zwitterionic monomers such as polyvinylpyrrolidone, dimethyl or diethylaminoethyl acrylate or methacrylate, alkyl acrylates or methacrylates, acrylamides or methacrylamides, or vinyl acetate.

By way of example, mention may be made of the copolymer of methyl methacrylate/methyl dimethylcarboxymethylaxmonioethyl methacrylate.

(6) chitosan-derived polymers containing monomer units corresponding to the following formulae:

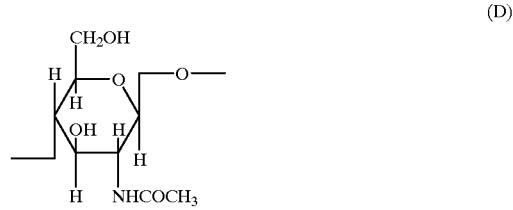

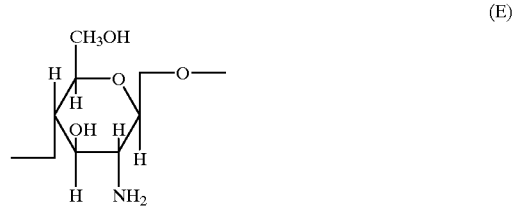

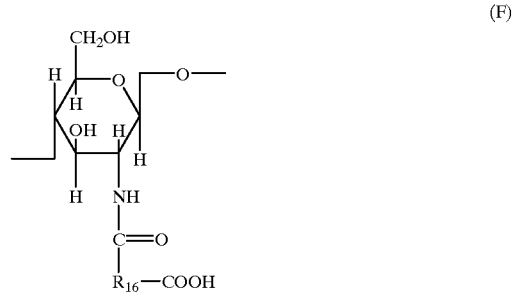

the unit D being present in proportions of between 0 and 30%, the unit E in proportions of between 5 and 50% and the unit F in proportions of between 30 and 90%, it being understood that in this unit F, $R_{16}$ represents a radical of formula:

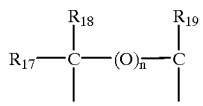

in which if n=0, $R_{17}$, $R_{18}$ and $R_{19}$, which may be identical or different, each represent a hydrogen atom, a methyl, hydroxyl, acetoxy or amino residue, a monoalkylamine residue or a dialkylamine residue optionally interrupted by one or more nitrogen atoms and/or optionally substituted by one or more amine, hydroxyl, carboxyl, alkylthio or sulphonic groups, an alkylthio residue in which the alkyl group bears an amino residue, at least one of the radicals $R_{17}$, $R_{18}$ and $R_{19}$ being, in this case, a hydrogen atom; or if n=1, $R_{17}$, $R_{18}$ and $R_{19}$ each represent a hydrogen atom, as well as the salts formed by these compounds with acids or bases.

(7) polymers derived from the N-carboxyalkylation of chitosan, such as N-carboxymethylchitosan or N-carboxybutylchitosan sold under the name "Evalsan" by the company Jan Dekker.

(8) polymers corresponding to the general formula (V), described in French patent 1,400,366:

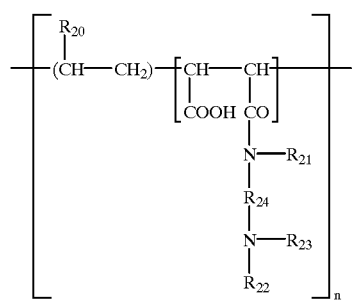

in which $R_{20}$ represents a hydrogen atom or a $CH_3O$, $CH_3CH_2O$ or phenyl radical, $R_{21}$ denotes hydrogen or a lower alkyl radical such as methyl or ethyl, $R_{22}$ denotes hydrogen or a lower alkyl radical such as methyl or ethyl, $R_{23}$ denotes a lower alkyl radical such as methyl or ethyl or a radical corresponding to the formula: $—R_{24}—N(R_{22})_2$, $R_{24}$ representing a $—CH_2—CH_2—$, $—CH_2—CH_2—CH_2—$ or $—CH_2—CH(CH_3)—$ group, $R_{22}$ having the meanings given above, as well as the higher homologues of these radicals and containing up to 6 carbon atoms.

(9) amphoteric polymers of the type —A—Z—A—Z, chosen from:
  a) polymers obtained by the action of chloroacetic acid or sodium chloroacetate on compounds containing at least one unit of formula:

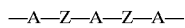 (VI)

where A denotes a radical

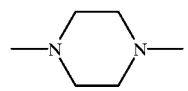

and Z denotes the symbol B or B', B and B', which may be identical or different, denote a divalent radical which is an alkylene radical with a straight or branched chain containing up to 7 carbon atoms in the main chain, unsubstituted or substituted with hydroxyl groups and also being able to contain oxygen, nitrogen or sulphur atoms, and 1 to 3 aromatic and/or heterocyclic rings, the oxygen, nitrogen and sulphur atoms being present in the form of ether, thioether, sulphoxide, sulphone, sulphonium, alkylamine or alkenylamine groups, and hydroxyl, benzylamine, amine oxide, guaternary ammonium, amide, imide, alcohol, ester and/or urethane groups.

b) polymers of formula:

—A—Z—A—Z— (VI')

where A denotes a radical

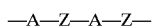

and Z denotes the symbol B or B' and at least once B', B having the meaning given above and B' being a divalent radical which is an alkylene radical containing a straight or branched chain having up to 7 carbon atoms in the main chain, unsubstituted or substituted with one or more hydroxyl radicals and containing one or more nitrogen atoms, the nitrogen atom being substituted with an alkyl chain optionally interrupted by an oxygen atom and necessarily containing one or more carboxyl functions or one or more hydroxyl functions and betainized by reaction with chloroacetic acid or sodium chloroacetate.

(10) copolymers of $(C_1-C_5)$alkyl vinyl ether/maleic anhydride partially modified by semiamidification with an N,N-dialkylaminoalkylamine such as N,N-dimethylaminopropylamine, or by semiesterification with an N,N-dialkanolamine. These copolymers can also contain other vinylic comonomers such as vinylcaprolactam.

The amphoteric polymers which are particularly preferred according to the invention are those of category (3) such as the copolymers whose CTFA name is octylacrylamide/acrylates/butylaminoethyl methacrylate copolymers such as the products sold under the name Amphomer or Lovocryl 47 by the company National Starch and those of category (5) such as the methacryloxyethyl-N,N-dimethylcarboxymethylbetaine/butyl methacrylate copolymer sold under the name Yukaformer AM 75 by the company Mitsubishi.

According to the invention, the amphoteric polymers can also be used in the form of a latex or a pseudolatex, that is to say in the form of an aqueous dispersion of insoluble polymer particles.

The (amphoteric polymer)/(grafted silicone polymer) ratio is preferably between 0.3 and 8.

According to the invention, the amphoteric polymer(s) can represent from 0.1% go 20% by weight, preferably from 0.2% to 15% by weight and even more preferably from 0.5% to 10% by weight, relative to the total weight of the final composition.

The cosmetically or dermatologically acceptable medium preferably consists of water or a mixture of water and cosmetically acceptable solvents such as monoalcohols, polyalcohols, glycol ethers or fatty acid esters, which can be used alone or as a mixture.

Mention may be made more particularly of lower alcohols such as ethanol and isopropanol, polyalcohols such as diethylene glycol, glycol ethers, glycol alkyl ethers or diethylene glycol alkyl ethers.

The grafted silicone polymers according to the invention can be dissolved in the said cosmetically acceptable medium or used in the form of an aqueous dispersion of particles.

The composition of the invention can also contain at least one additive chosen from thickeners, fatty acid esters, fatty acid esters of glycerol, silicones, surfactants, fragrances, preserving agents, sunscreens, proteins, vitamins, polymers, plant, animal, mineral or synthetic oils or any other additive conventionally used in the cosmetic field.

These additives are present in the composition according to the invention in proportions which can range from 0 to 20% by weight relative to the total weight of the composition. The precise amount of each additive depends on its nature and is determined readily by those skilled in the art.

Needless to say, a person skilled in the art will take care to select the optional compound(s) to be added to the composition according to the invention such that the advantageous properties intrinsically associated with the composition in accordance with the invention are not, or are not substantially, adversely affected by the addition envisaged.

The compositions according to the invention can be in the form of a gel, a milk, a cream, a relatively thickened lotion or a mousse.

The compositions according to the invention are used as rinse-out products or as leave-in products, in particular to wash, care for or condition keratin substances such as human hair, to maintain the hairstyle or to shape the hairstyle.

These compositions are more particularly hairsetting lotions, blow-drying lotions, fixing compositions (lacquers) and styling compositions. The lotions can be packaged in various forms, in particular in vapourizers, pump-dispenser bottles or in aerosol containers in order to ensure application of the composition in vapourized form or in the form of a mousse. Such packaging forms are indicated, for example, when it is desired to obtain a spray, a lacquer or a mousse for fixing or treating the hair.

The compositions can also be shampoos, rinse-out or leave-in compositions, to be applied before or after shampooing, dyeing, bleaching, permanent-waving or straightening the hair.

When the composition according to the invention is packaged in aerosol form in order to obtain a lacquer or an aerosol mousse, it comprises at least one propellant which can be chosen from volatile hydrocarbons such as n-butane, propane, isobutane, pentane, a chloro and/or fluoro hydrocarbon, and mixtures thereof. Carbon dioxide, nitrous oxide, dimethyl ether, nitrogen or air, which is compressed, and mixtures thereof, can also be used as propellant.

Another subject of the invention is a process for treating keratin substances such as human hair, which consists in applying a composition as defined above to the hair and then optionally in rinsing with water.

The invention will now be illustrated more fully with the aid of the examples which follow, which should not be considered as limiting it to the embodiments described.

EXAMPLES

Example 1
Styling Spray in a Pump-dispenser Bottle

| | |
|---|---|
| Grafted silicone polymer of formula (I) of polymethyl/methylsiloxane structure containing 3-propylthio polyisobutyl methacrylate groups in solution in a cyclic volatile silicone | 3 g AM |
| Acrylic acid/methyl methacrylate/N-tert-butylaminoethyl methacrylate/N-octylacrylamide/hydroxypropyl methacrylate copolymer (Amphomer LV 71 from National Starch) | 4 g AM |
| Aminomethylpropanol, 100% neutralization of the silicone polymer qs | 100 g |
| Ethanol qs | |

Example 2
Shampooing

| | |
|---|---|
| Grafted silicone polymer of formula (I) of polymethyl/methylsiloxane structure containing a 3-propylthio poly(methacrylic acid) group and 3-propylthio polymethyl methacrylate groups | 1 g AM |
| Methacryloxyethyl-N,N-dimethylcarboxymethylbetaine/butyl methacrylate copolymer sold under the name Yukaformer AM 75 by the company Mitsubishi | 1.5 g AM |
| Lauryl monosulphosuccinate ($C_{12}/C_{14}$; 70/30) oxyethylenated with 3 mol of ethylene oxide, in the form of the disodium salt, as an aqueous 40% solution sold under the name Setacin 103 Special by the company Zschimmen Schwarz | 12 g AM |
| Cocoylamidopropylbetaine/glyceryl monolaurate mixture (25/5) as an aqueous 30% solution | 8 g AM |
| Sodium olefin sulphonate sold under the name Hostapur OS by the company Hoechst | 8 g MA |
| Sequestering agent, fragrance, preserving agent | qs |
| NaOH qs | pH 7.7 |
| Water qs | 100 g |

We claim:

1. A cosmetic or dermatological composition comprising, in a cosmetically or dermatologically acceptable medium,
   (a) at least one grafted silicone polymer containing a polysiloxane skeleton grafted with at least one non-silicone organic monomer selected from anionic, amphoteric and nonionic monomers and
   (b) at least one amphoteric polymer,
   wherein said at least one amphoteric polymer and at least one grafted silicone polymer are present in a ratio ranging from 0.25:1 to 15:1, wherein said (a) is different from said (b).

2. A cosmetic or dermatological composition according to claim 1, wherein said at least one grafted silicone polymer comprises a polysiloxane skeleton on which is grafted, inside said skeleton as well as, optionally, on at least one of its ends, said at least one non-silicone organic monomer.

3. A cosmetic or dermatological composition according to claim 1, wherein said at least one grafted silicone polymer is obtained by radical copolymerization between
   (a) at least one non-silicone organic monomer having ethylenic unsaturation selected from anionic and hydrophobic monomers, and,
   (b) at least one polysiloxane having, in its skeleton, at least one functional group capable of reacting with said ethylenic unsaturation of said at least one non-silicone organic monomer.

4. A cosmetic or dermatological composition according to claim 3, wherein said at least one non-silicone anionic organic monomer is selected from linear and branched unsaturated carboxylic acids, optionally partially and totally neutralized in the form of a salt.

5. A cosmetic or dermatological composition according to claim 3, wherein said at least one non-silicone anionic organic monomer is selected from acrylic acid, methacrylic acid, maleic acid, maleic anhydride, itaconic acid, fumaric acid, crotonic acid, alkali-metal salts of the above acids, alkaline-earth metal salts of the above acids and ammonium salts of the above acids.

6. A cosmetic or dermatological composition according to claim 3, wherein said at least one non-silicone hydrophobic organic monomer is selected from acrylic acid esters of an alkanol and methacrylic acid esters of an alkanol.

7. A cosmetic or dermatological composition according to claim 6, wherein said alkanol is $C_1$–$C_{18}$.

8. A cosmetic or dermatological composition according to claim 7, wherein said alkanol is $C_1$–$C_{12}$.

9. A cosmetic or dermatological composition according to claim 3, wherein said at least one non-silicone hydrophobic organic monomer is selected from isooctyl(meth)acrylate, isononyl(meth)acrylate, 2-ethylhexyl(meth)acrylate, lauryl (meth)acrylate, isopentyl(meth)acrylate, n-butyl(meth) acrylate, isobutyl(meth)acrylate, methyl(meth)acrylate, tert-butyl(meth)acrylate, tridecyl(meth)acrylate and stearyl (meth)acrylate.

10. A cosmetic or dermatological composition according to claim 1, wherein said at least one grafted silicone polymer comprises, on the main polysiloxane skeleton, at least one non-silicone organic group of anionic nature obtained by radical (homo)polymerization of at least one non-silicone anionic monomer of unsaturated carboxylic acid type, partially or totally neutralized in the form of a salt.

11. A cosmetic or dermatological composition according to claim 1, wherein said at least one grafted silicone polymer is selected from silicone polymers containing in their structure the unit of formula (I):

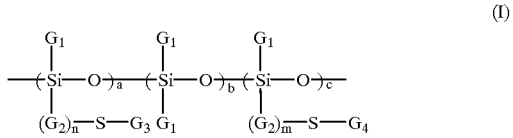

in which:
the radicals $G_1$ each independently represent hydrogen or a $C_1$–$C_{10}$ alkyl radical or a phenyl radical;
the radicals $G_2$ each independently represent a divalent $C_1$–$C_{10}$ alkylene group;
$G_3$ represents a polymer residue resulting from the (homo)polymerization of at least one anionic monomer containing ethylenic unsaturation;
$G_4$ represents a polymer residue resulting from the (homo)polymerization of at least one hydrophobic monomer containing ethylenic unsaturation;
m and n are equal to 0 or 1;
a is an integer ranging from 0 to 50;
b is an integer ranging from 10 to 350;
c is an integer ranging from 0 to 50;
with the proviso that one of a and c is not 0.

12. A cosmetic or dermatological composition according to claim 11, wherein said unit of formula (I) has at least one of the following characteristics:
the radicals $G_1$ denote a $C_1$–$C_{10}$ alkyl radical;
n is non-zero and the radicals $G_2$ represent a divalent $C_1$–$C_3$ radical;

$G_3$ represents a polymeric residue resulting from the (homo)polymerization of at least one carboxylic acid monomer containing ethylenic unsaturation; and
$G_4$ represents a polymeric residue resulting from the (homo)polymerization of at least one $C_1$–$C_{10}$ alkyl (meth)acrylate monomer.

13. A cosmetic or dermatological composition according to claim 11, wherein said unit of formula (I) simultaneously has the following characteristics:
the radicals $G_1$ denote a methyl radical;
n is non-zero and the radicals $G_2$ represent a propylene radical;
$G_3$ represents a polymeric residue resulting from the (homo)polymerization of at least one monomer selected from acrylic acid and methacrylic acid;
$G_4$ represents a polymeric residue resulting from the (homo)polymerization of at least one monomer selected from isobutyl and methyl (meth)acrylate monomers.

14. A cosmetic or dermatological composition according to claim 1, wherein the number-average molecular mass of said at least one grafted silicone polymer ranges from 10,000 to 1,000,000.

15. A cosmetic or dermatological composition according to claim 14, wherein said number-average molecular mass of said at least one grafted silicone polymer ranges from 10,000 to 100,000.

16. A cosmetic or dermatological composition according to claim 1, wherein said at least one grafted silicone polymer is present in a concentration ranging from 0.01 to 20% by weight relative to the total weight of said composition.

17. A cosmetic or dermatological composition according to claim 16, wherein said at least one grafted silicone polymer is present in a concentration ranging from 0.1 to 15% by weight relative to the total weight of said composition.

18. A cosmetic or dermatological composition according to claim 17, wherein said at least one grafted silicone polymer is present in a concentration ranging from 0.5 to 10% by weight relative to the total weight of said composition.

19. A cosmetic or dermatological composition according to claim 1, wherein said at least one amphoteric polymer is selected from polymers containing units (A) and (B) randomly distributed in the polymer chain and wherein:
(A) denotes a unit derived from a monomer containing at least one basic nitrogen atom and (B) denotes a unit derived from an acidic monomer containing at least one group selected from carboxylic and sulphonic groups; or
(A) and (B) denote a cationic polymer chain containing primary, secondary, tertiary or quaternary amine groups in which at least one of the amine groups bears a carboxylic or sulphonic group connected via a hydrocarbon radical; or
(A) and (B) form part of a polymer chain containing an α,β-dicarboxylic ethylene unit in which one of the carboxylic groups has been reacted with a polyamine containing one or more primary or secondary amine groups; or
(A) and (B) denote groups derived from carboxybetaine or sulphobetaine zwitterionic monomers.

20. A cosmetic or dermatological composition according to claim 1, wherein said at least one amphoteric polymer is selected from:
(1) polymers resulting from the copolymerization of a monomer derived from a vinyl compound bearing a carboxylic group, and of a basic monomer derived from a substituted vinyl compound containing at least one basic atom;

(2) polymers derived from diallyldialkylammonium and from at least one anionic monomer;

(3) polymers containing units derived:
   a) from at least one monomer selected from acrylamides and methacrylamides substituted on the nitrogen with an alkyl radical,
   b) from at least one acidic comonomer containing one or more reactive carboxylic groups, and
   c) from at least one basic comonomer;

(4) partially and totally alkylated and crosslinked polyamino amides derived from polyamino amides of the formula:

$$\text{\{CO—R}_{10}\text{—CO—Z\}} \tag{II}$$

in which:

$R_{10}$ represents a divalent radical derived from a saturated dicarboxylic acid, from an aliphatic mono- or dicarboxylic acid containing an ethylenic double bond, from an ester of a lower alkanol having 1 to 6 carbon atoms of said acids or from a radical derived from the addition of any one of said acids to a bis-primary or bis-secondary amine, and Z denotes a radical of a bis-primary, mono- or bis-secondary polyalkylene polyamine, wherein these polyamino amides are crosslinked by addition of a difunctional crosslinking agent selected from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof;

(5) polymers containing zwitterionic units of formula (IV):

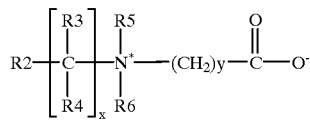

in which:

$R_2$ denotes a polymerizable unsaturated group, x and y represent an integer ranging from 1 to 3, $R_3$ and $R_4$ independently represent hydrogen, methyl, ethyl or propyl, $R_5$ and $R_6$ independently represent a hydrogen atom or an alkyl radical wherein the sum of the carbon atoms in $R_5$ and $R_6$ does not exceed 10;

wherein said polymers containing zwitterionic units of formula (IV) optionally also contain units derived from non-zwitterionic monomers;

(6) chitosan-derived polymers containing monomer units corresponding to the following formulae:

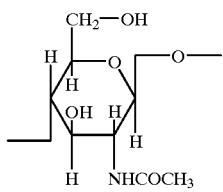

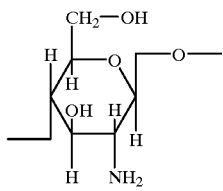

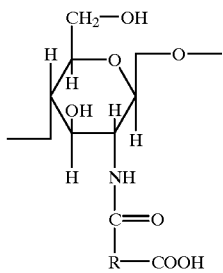

in which:

the unit A is present in a concentration ranging from 0 to 30%, the unit B is present in a concentration ranging from 5 to 50%, and the unit C is present in a concentration ranging from 30 to 90%, wherein in said unit C, R represents a radical of formula:

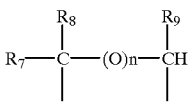

in which if n=0, $R_7$, $R_8$ and $R_9$ each independently represents a hydrogen atom, a methyl, hydroxyl, acetoxy or amino residue, a monoalkylamine residue or a dialkylamine residue optionally interrupted by one or more nitrogen atoms and/or optionally substituted by one or more amine, hydroxyl, carboxyl, alkylthio or sulphonic groups, or an alkylthio residue in which the alkyl group bears an amino residue, wherein in this case, at least one of the radicals $R_7$, $R_8$ and $R_9$ is a hydrogen atom; or if n=1, $R_7$, $R_8$ and $R_9$ each independently represents a hydrogen atom, and the salts formed by said chitosan-derived polymers with acids or bases;

(7) polymers derived from the N-carboxyalkylation of chitosan;

(8) polymers corresponding to the formula (V),

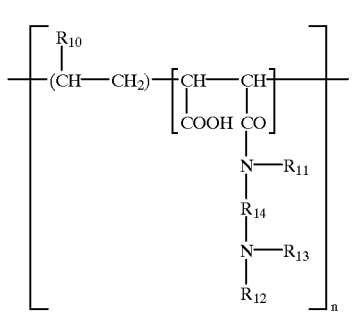

in which:

$R_{10}$ represents a hydrogen atom or a $CH_3O$, $CH_3CH_2O$ or phenyl radical, $R_{11}$ denotes hydrogen or a lower alkyl radical, $R_{12}$ denotes hydrogen or a lower alkyl radical, $R_{13}$ denotes a lower alkyl radical or a radical corresponding to the formula:

$R_{14}$—$N(R_{12})_2$, wherein $R_{14}$ represents a —$CH_2$—$CH_2$—,
—$CH_2$—$CH_2$—$CH_2$— or —$CH_2$—$CH(CH_3)$— group, $R_{12}$ denotes hydrogen or a lower alkyl radical, as well as the higher homologues of these radicals and containing up to 6 carbon atoms:

(9) amphoteric polymers of the type —A—Z—A—Z, selected from:

a) polymers obtained by the action of chloroacetic acid or sodium chloroacetate on compounds containing at least one unit of formula:

—A—Z—A—Z—A—  (VI)

in which:

A independently denotes a radical

and

Z denotes the symbol B or B', wherein B and B' each independently denotes a divalent alkylene radical with a straight or branched chain containing up to 7 carbon atoms in the main chain, unsubstituted or substituted with hydroxyl groups and also being able to contain oxygen, nitrogen or sulphur atoms, and from 1 to 3 aromatic and/or heterocyclic rings, the oxygen, nitrogen and sulphur atoms being present in the form of ether, thioether, sulphoxide, sulphone, sulphonium, alkylamine or alkenylamine groups, and hydroxyl, benzylamine, amine oxide, quaternary ammonium, amide, imide, alcohol, ester and/or urethane groups;

b) polymers of formula:

—A—Z—A—Z—  (VI')

in which:

A independently denotes a radical

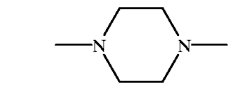

and

Z denotes the symbol B or B' wherein B' is present at least once and B denotes the same radical as defined in selection (9)(a) and B' is a divalent alkylene radical containing a straight or branched chain having up to 7 carbon atoms in the main chain, unsubstituted or substituted with one or more hydroxyl radicals and containing one or more nitrogen atoms, the nitrogen atom being substituted with an alkyl chain optionally interrupted by an oxygen atom and necessarily containing one or more carboxyl functions or one or more hydroxyl functions and betainized by reaction with chloroacetic acid or sodium chloroacetate; and

(10) copolymers of $(C_1-C_5)$alkyl vinyl ether/maleic anhydride partially modified by semiamidification with an N,N-dialkylaminoalkylamine, or by semiesterification with an N,N-dialkanolamine, wherein said copolymers also optionally contain other vinylic comonomers.

21. A cosmetic or dermatological composition according to claim 20, wherein said carboxylic group in selection (1) is selected from acrylic acid, methacrylic acid, maleic acid and a-chloroacrylic acid and further wherein said basic monomer in selection (1) is selected from dialkylaminoalkyl methacrylates and acrylates and dialkylaminoalkyl methacrylamides and acrylamides.

22. A cosmetic or dermatological composition according to claim 20, wherein said polymers derived from diallyldialkylammonium in selection (2) are selected from polymers containing from 60 to 99% by weight of units derived from a quaternary diallyldialkylammonium monomer in which the alkyl groups are selected, independently, from alkyl groups having from 1 to 18 carbon atoms and in which the anion is derived from an acid having an ionization constant of greater than $10^{-13}$ and further containing from 1 to 40% by weight relative to the total weight, of an anionic monomer selected from acrylic acid and methacrylic acid, and wherein the molecular weight of said polymers ranges from 50,000 to 10,000,000, measured by gel permeation chromatography.

23. A cosmetic or dermatological composition according to claim 20, wherein said at least one basic comonomer in selection (3)(c) is selected from esters containing primary, secondary, tertiary and quaternary amine substituents of acrylic acid and methacrylic acid and the quaternization product of dimethylaminoethyl methacrylate with dimethyl or diethyl sulphate.

24. A cosmetic or dermatological composition according to claim 20, wherein Z in selection (4) represents:

a) in proportions of from 60 to 100 mol %, the radical (III)

—NH—[(CH_2)_8—NH]_n—  (III)

in which x=2 and n=2 or 3 or alternatively x=3 and n=2, and wherein said radical (III) is derived from diethylonetriamine, trethylenetetraamine or dipropylenetriamine;

b) in proportions of from 0 to 40 mol %, the radical (III) above, in which x=2 and n=1 and wherein said radical (III) is derived from ethylenediamine, or the radical derived from piperazine:

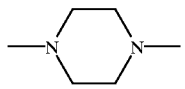

and c) in proportions of 0 to 20 mol %, the radical —NH—(CH$_2$)$_8$—NH— derived from hexamethylenediamine.

25. A cosmetic or dermatological composition according to claim 20, wherein R$_2$ in selection (5) denotes an acrylate, methacrylate, acrylamide or methacrylamide group.

26. A cosmetic or dermatological composition according to claim 20, wherein R$_{11}$ in selection (8) denotes methyl or ethyl.

27. A cosmetic or dermatological composition according to claim 20, wherein R$_{12}$ in selection (8) denotes methyl or ethyl.

28. A cosmetic or dermatological composition according to claim 20, wherein R$_{13}$ in selection (8) denotes methyl or ethyl.

29. A cosmetic or dermatological composition according to claim 20, wherein said N,N-dialkylaminoalkylamine in selection (10) is selected from N,N-dimethylaminopropylamine and wherein said copolymers of selection (10) optionally also contain vinylcaprolactam.

30. A cosmetic or dermatological composition according to claim 1, wherein said ratio of said at least one amphoteric polymer to said at least one grafted silicone polymer ranges from 0.3:1 to 8:1.

31. A cosmetic or dermatological composition according to claim 1, wherein said at least one amphoteric polymer is present in a concentration ranging from 0.1 to 20% by weight, relative to the total weight of said composition.

32. A cosmetic or dermatological composition according to claim 31, wherein said at least one amphoteric polymer is present in a concentration ranging from 0.2 to 15% by weight, relative to the total weight of said composition.

33. A cosmetic or dermatological composition according to claim 32, wherein said at least one amphoteric polymer is present in a concentration ranging from 0.5 to 10% by weight, relative to the total weight of said composition.

34. A cosmetic or dermatological composition according to claim 1, wherein said cosmetically or dermatologically acceptable medium comprises water or a mixture of water and at least one cosmetically acceptable solvent.

35. A cosmetic or dermatological composition according to claim 34, wherein said at least one cosmetically acceptable solvent is selected from monoalcohols, polyalcohols, glycol ethers and fatty acid esters.

36. A cosmetic or dermatological composition according to claim 1, wherein said at least one grafted silicone polymer is dissolved in the cosmetically or dermatologically acceptable medium or is in the form of an aqueous dispersion of particles.

37. A cosmetic or dermatological composition according to claim 1 wherein said composition is a treatment composition for a keratin substance.

38. A cosmetic or dermatological composition according to claim 37, wherein said keratin substance is human hair.

39. A cosmetic or dermatological composition according to claim 1, wherein said composition is in the form of a gel, a milk, a cream, a thickened lotion or a foam.

40. A cosmetic or dermatological composition according to claim 1, wherein said composition further comprises at least one additive selected from thickeners, fatty acid esters, fatty acid esters of glycerol, silicones, surfactants, fragrances, preserving agents, sunscreens, proteins, vitamins, different polymers, plant, animal, mineral and synthetic oils and any other suitable cosmetic additive.

41. A cosmetic or dermatological composition according to claim 1, wherein said composition is a styling product.

42. A cosmetic or dermatological composition according to claim 1, wherein said composition is a hair product to be applied before or after shampooing, dyeing, bleaching, permanent-waving or straightening the hair.

43. A cosmetic or dermatological composition according to claim 42, wherein said hair product is selected from shampoos and rinse-out and leave-in hair products.

44. A cosmetic or dermatological composition according to claim 1, wherein said composition is packaged in the form of a vaporizer, a pump-dispenser bottle or in an aerosol container.

45. A non-therapeutic process for treating a keratin substance comprising applying a composition according to claim 1 to said keratin substance, and then optionally rinsing with water.

46. A non-therapeutic process according to claim 45, wherein said keratin substance is human hair.

* * * * *

UNITED STATES PATENT AND TRADEMARK OFFICE
CERTIFICATE OF CORRECTION

PATENT NO. : 5,976,517
DATED : November 2, 1999
INVENTOR(S) : Dubief et al.

Page 1 of 1

It is certified that error appears in the above-identified patent and that said Letters Patent is hereby corrected as shown below:

<u>Column 16,</u>
Line 30, change "a" to -- $\alpha$ --.

Signed and Sealed this

Twenty-third Day of April, 2002

Attest:

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO.   : 5,976,517
DATED        : November 2, 1999
INVENTOR(S)  : Dubief et al.

It is certified that error appears in the above-identified patent and that said Letters Patent is hereby corrected as shown below:

Column 13,
In Structure (IV) change "N*" to -- N⁻ --.

Column 16,
Line 64, "trethylenetetramine" to -- triethylenetetraamine --.

Signed and Sealed this

Twenty-sixth Day of November, 2002

Attest:

JAMES E. ROGAN
Attesting Officer    Director of the United States Patent and Trademark Office